US011657175B2

(12) United States Patent
Cohen et al.

(10) Patent No.: US 11,657,175 B2
(45) Date of Patent: May 23, 2023

(54) PATIENT MEDICAL DATA ACQUISITION SYSTEM AND METHOD USING AN EXTERNAL DEVICE

(71) Applicant: Algotec Systems Ltd., Rochester, NY (US)

(72) Inventors: Meir Cohen, Givat Shmuel (IL); David Altal, Holon (IL); Guy Engelhard, Kiryat Ono (IL); Guy Gelles, Herzilya (IL); Ron Kimchi, Tel Aviv (IL); Erez Bibi, Raanana (IL); Kiran Krishnamurthy, Westford, MA (US); Menashe Benjamin, Raanana (IL)

(73) Assignee: PHILIPS MEDICAL SYSTEMS TECHNOLOGIES LTD, Haifa (IL)

( * ) Notice: Subject to any disclaimer, the term of this patent is extended or adjusted under 35 U.S.C. 154(b) by 589 days.

(21) Appl. No.: 15/275,517

(22) Filed: Sep. 26, 2016

(65) Prior Publication Data
US 2017/0242963 A1    Aug. 24, 2017

Related U.S. Application Data

(60) Provisional application No. 62/345,943, filed on Jun. 6, 2016, provisional application No. 62/298,664, filed on Feb. 23, 2016.

(51) Int. Cl.
| | | |
|---|---|---|
| G06F 21/62 | (2013.01) | |
| G16H 10/60 | (2018.01) | |
| H04L 67/06 | (2022.01) | |
| G16H 30/20 | (2018.01) | |
| H04L 67/306 | (2022.01) | |

(52) U.S. Cl.
CPC ......... *G06F 21/6245* (2013.01); *G16H 10/60* (2018.01); *G16H 30/20* (2018.01); *H04L 67/06* (2013.01); *H04L 67/306* (2013.01)

(58) Field of Classification Search
CPC .......... G06Q 50/22–24; G06F 21/6245; G06F 19/321; G16H 10/60; G16H 30/20; H04L 67/06; H04L 67/306
See application file for complete search history.

(56) References Cited

U.S. PATENT DOCUMENTS 7,027,871 B2 *   4/2006   Burnes ................. A61B 5/0031
                                                        607/32
7,029,443 B2 *   4/2006   Kroll .................... A61B 5/0452
                                                        600/365

(Continued)

*Primary Examiner* — Devin C Hein (57) ABSTRACT

A method of sending a medical data file from an external device to a computer system and storing the data file associated with a patient's identity, comprising: a) the computer system receiving information that a data file to be sent to the computer system from the external device (or from one of a set of external devices) is to be associated with the patient's identity; b) sending the data file from the external device to the computer system, with the data file identified as coming from the external device; c) the computer system finding the patient's identity from the identification of the image file as coming from the external device, and from the information that a data file to be associated with the patient's identity was to be sent from that external device; and d) the computer system storing the data file, associating the data file with the patient's identity.

20 Claims, 6 Drawing Sheets

(56) References Cited

U.S. PATENT DOCUMENTS

| | | | |
|---|---|---|---|
| 7,207,947 B2* | 4/2007 | Koh | A61N 1/36557 600/529 |
| 7,989,757 B2* | 8/2011 | Al-Moosawi | A61B 5/0064 250/234 |
| 8,395,498 B2* | 3/2013 | Gaskill | G16H 40/67 340/539.12 |
| 8,396,803 B1* | 3/2013 | Dala | G06Q 50/22 705/52 |
| 8,679,014 B2* | 3/2014 | Bennett | A61B 1/00016 600/301 |
| 8,694,600 B2* | 4/2014 | Gaines | A61B 5/0026 709/217 |
| 8,799,011 B2* | 8/2014 | Wilson | G16H 10/60 705/2 |
| 9,223,932 B1 | 12/2015 | Rice et al. | |
| 9,619,616 B2* | 4/2017 | Raduchel | G16H 10/60 |
| 2003/0009154 A1* | 1/2003 | Whitman | G06Q 10/087 606/1 |
| 2005/0043583 A1* | 2/2005 | Killmann | A61B 1/00016 600/109 |
| 2009/0023422 A1* | 1/2009 | MacInnis | A61B 5/681 455/411 |
| 2009/0164253 A1 | 6/2009 | Lyshkow | |
| 2011/0313774 A1* | 12/2011 | Ji | G06Q 10/00 704/E11.001 |
| 2012/0120220 A1 | 5/2012 | Al-Moosawi | |
| 2012/0185929 A1* | 7/2012 | Yariv | H04L 63/0227 726/11 |
| 2013/0282400 A1* | 10/2013 | Al-Moosawi | G16H 10/60 705/3 |
| 2014/0067426 A1* | 3/2014 | Neff | G16H 40/63 705/3 |
| 2014/0278530 A1 | 9/2014 | Bruce et al. | |
| 2015/0026175 A1 | 1/2015 | Nuggehalli et al. | |
| 2015/0193579 A1 | 7/2015 | Bruce et al. | |
| 2016/0113509 A1* | 4/2016 | Gross | G06T 3/40 600/474 |
| 2019/0254600 A1* | 8/2019 | Moon | A61B 5/6824 |
| 2020/0069247 A1* | 3/2020 | Hunter | A61B 17/00 |

* cited by examiner

PATIENT MEDICAL DATA ACQUISITION SYSTEM AND METHOD USING AN EXTERNAL DEVICE

CROSS REFERENCE TO RELATED APPLICATIONS

This application claims the benefit of U.S. Provisional application U.S. Ser. No. 62/298,664, provisionally filed on Feb. 23, 2016, entitled "PATIENT IMAGING ACQUISITION USING MOBILE DEVICE CAMERA", in the names of Cohen et al., which is incorporated herein by reference in its entirety.

This application claims the benefit of U.S. Provisional application U.S. Ser. No. 62/345,943, provisionally filed on Jun. 6, 2016, entitled "PATIENT MEDICAL DATA ACQUISITION SYSTEM AND METHOD USING AN EXTERNAL DEVICE", in the names of Cohen et al., which is incorporated herein by reference in its entirety.

FIELD OF THE INVENTION

The present disclosure, in some embodiments thereof, relates to a method of acquiring medical data from a patient using a possibly insecure external device, sending the data over a possibly insecure communications link to a medical computer system, and storing the data in the computer system associated with the identity of the patient; more particularly, but not exclusively, to the case where the medical data comprises medical images, and the external device is a mobile device.

BACKGROUND

Hospitals, health maintenance organizations, and other facilities that provide medical care for a large number of patients often store medical data for their patients in a medical computer system. In such a system, one or more databases contains medical data files, for example medical test results and other text-based files in an electronic medical records (EMR) database, and medical images in a picture archiving and communication system (PACS), each file associated with a patient ID indicating which patient it pertains to. Physicians and other medical personnel who are involved in providing medical care for a given patient can access the medical files for that patient, through the medical computer system, for example through a server connecting the databases to personal computers used by the medical personnel. Such medical files are generally considered confidential, and the computer system provides a desired level of security to prevent unauthorized persons from obtaining the medical data files, and associated patient IDs, stored in the database. Sometimes medical personnel will obtain medical data from a patient using an external device, not part of the secure medical computer system, for example using a mobile device to make a medical image of the patient. It is desirable to add such data to the computer system databases, associated with the patient ID, so it will be readily available in the future to anyone using the computer system that is treating that patient. But it is desirable to do this without compromising confidentiality by sending the data, associated with the patient ID, over a possibly insecure communications link, and without the need for the medical personnel who obtain the data to go through a time-consuming procedure for entering the data and associated patent ID into the database, for example by transferring the data manually from the external device to the computer system.

U.S. 2015/0193579 (Bruce et al.) discusses the problem of "ensuring that medical imaging transported or acquired on mobile devices is associated with the correct patient and efficiently and universally archived within the medical record." A method is described, in which "the first client computer system can provide the second client computer system with information that is sufficient to identify a computer session in which the medical imaging data is being exchanged with the server computer system . . . . Identifying the computer session allows the second client computer system to provide medical imaging data for association with the patient without receiving the patient's private information."

In describing a variation on this method, Bruce et al state that "the desktop computer system need not generate and display an identifier [of the computer session]. Instead, exchange of the medical imaging data can occur based on the identity of the user . . . . [T]he mobile computer system queries the server computer system about any active computer sessions associated with the identity of the user . . . . [T]he server computer system provides information about any active sessions associated with the identity of the user [and] the mobile computer systems displays the available sessions . . . . A user of the mobile computer system selects an appropriate session, e.g., the session in which the user is exchanging medical imaging data between the desktop computer system and the server computer system . . . . [T]he mobile computer system receives medical imaging data from an external source [and] associates the computer session identifier . . . with the received medical imaging data . . . . [T]he mobile computer system transmits the medical imaging data to the server computer system [and] the server computer system associates the received medical imaging data with the patient-related information exchanged in the computer session."

U.S. Pat. No. 9,223,932 (Rice et al) describes a method of acquiring medical image data for a subject having a subject medical record and subject identifying information. The method includes capturing medical image data related to the subject with a mobile wireless-communication optical-imaging device. A program is provided that includes a request for subject identifying information. Data derived from the medical image data, and the subject identifying information, are wirelessly transmitted from the mobile device to a second, separate device.

U.S. 2009/0164253 (Lyshkow) describes methods of securely directing the transfer of medical information between a smartphone and a storage site of patient information, or between two smartphones, to expedite the flow of patient information between physicians, wherever they are located, and repositories of patient information, and to allow an individual to securely transport their Personal Health Record and store it on their smartphone in its original DICOM or HL7 format.

U.S. 2012/0120220 (Al-Moosawi) describes a mobile device and a method for capturing and transmitting medical images from the mobile device to a server. The method includes acquiring an image of a wound on a patient's body, and transmitting to the server, in response to a user request, the acquired image, and location information indicating where on the patient's body the wound is located. If a caregiver uses the same device to capture and upload wound images for multiple patients, then the caregiver may enter the patient's name in the device, before uploading an image.

U.S. 2014/0278530 (Bruce et al) describes methods for associating received medical imaging data with stored medical imaging data of the same patient. Medical imaging data for a patient is received from a client device. The medical imaging data includes metadata associated with the patient, including personal information about the patient. The received metadata is compared with existing metadata associated with multiple existing patients to identify a subset of the existing patients who may be a potential match to the patient. Selection of an existing patient from among the subset is requested. When received, the medical imaging data is associated with the existing patient.

Reference is also made to U.S. 2015/0026175 (Nuggehalli et al).

SUMMARY

An aspect of some embodiments of the disclosure concerns a method for a medical computer system to associate a patient identity with medical data received from an external device, using only information about the identity of the external device and information already stored within the computer system. In particular, the method does not require the computer system to send new information to the external device each time the method is used for a different patient.

There is thus provided, in accordance with an embodiment of the disclosure, a method of sending a medical data file from an external device to a computer system and storing the data file associated with an identity of a patient, the method comprising: a) the computer system receiving and storing information that a data file to be sent to the computer system from one of a set of one or more external devices is to be associated with the identity of the patient; b) sending the data file from one of the set of one or more external devices to the computer system, with the data file identified at least as coming from one of the set of one or more external devices; c) the computer system finding the identity of the patient from the identification of the image file as coming from one of the set of one or more external devices, and from the stored information that a data file to be associated with the identity of that patient was to be sent from one of that set of one or more external devices; and d) the computer system storing the data file in a data storage device, associating the data file with the identity of the patient.

Optionally, the computer system sends to the external device that sends the data file information on how to send data files from the external device to the computer system, before sending the data file; the external device uses the information on how to send data files, when sending the data file; and the method also includes repeating (a) through (d) for a data file to be associated with an identity of a different patient, again using the information on how to send data files, when sending the data file to be associated with the different patient.

Optionally, the computer system sending information to the external device comprises the computer system displaying a machine readable visual code to the external device, and the external device scanning the machine readable visual code.

Optionally, the method also comprises: storing in the computer system a list of device identifiers for one or more external devices to be used by a user for acquiring data files pertaining to patients, before doing (a); and repeating (a) through (d) one or more times; wherein, for each time (a) through (d) are done, one of said external devices is used as the external device from which the data file is sent, and wherein, for each time, (a) comprises either the user selecting one or more external devices from the list as the set of one or more external devices, or the computer system selecting all the external devices as the set of one or more external devices.

Optionally, the method also comprises, for each of the external devices on the list, the computer system displaying a machine readable visual code to the external device, the external device scanning the machine readable visual code, and the external device sending its device identifier to the computer system in response to the machine readable visual code.

Optionally, the computer system receiving and storing information comprises a user of the computer system entering on the computer system an indication of the identity of the patient, as part of a procedure for getting access to medical records of the patient, for the computer system to record that the user was dealing with the patient at that time, or both.

Optionally, the computer system receiving and storing information comprises a user of the computer system entering an indication of the identity of the patient only once, for sending that medical data file.

Optionally, the user enters the indication of the identity of the patient on the computer system, and not on the external device that sends the medical data file to the computer system.

Optionally, the computer system receiving and storing information comprises the user identifying the external device to the computer system.

Optionally, sending the data file from the external device to the computer system is done automatically by the external device after the data is acquired.

Optionally, the method also includes the external device acquiring data for the data file.

Optionally, the data file is an image file, and acquiring the data comprises using a camera controlled by the external device to make an image of the patient.

Alternatively, the data file comprises data of the patient taken with a medical instrument and communicated to the external device.

Optionally, the data comprises one or more of pulse data, blood pressure data, body temperature data, EKG data, EEG data, electrical impedance data, magnetic field data, blood analysis data, spectroscopic data of body tissue, auditory data of the heart, auditory data of the lungs, NMR data, and DNA sequence data.

Optionally, the data comprises data of a medical imaging modality.

Optionally, the computer system uses security procedures to prevent unauthorized transfer or copying of confidential patient medical information to outside the computer system, and the external device is outside the computer system.

Optionally, the computer system comprises a server connected to a plurality of peripheral computers used by a plurality of different users, and providing the information to the computer system comprises a user providing the information to one of the peripheral computers.

Optionally, the computer system uses security features to prevent the unauthorized transfer outside the computer system of medical data identified as pertaining to a patient, and the external device is outside the computer system.

Optionally, sending the data file comprises sending the data file without information that directly or indirectly identifies the patient, other than information that identifies the data file as coming from the external device.

Optionally, the external device that sends the data file to the computer system has no information directly or indirectly associating the data file with the identity of the patient, when the data file is sent.

Optionally, the external device that sends the data file has no information about the identity of the patient, when the data file is sent.

There is further provided, in accordance with an exemplary embodiment of the disclosure, a medical data acquisition system for acquiring patient medical records and storing them in a data storage device associated with an identity of one of a plurality of patients, the acquisition system comprising: a computer or a plurality of connected computers, running data acquisition software comprising: a) a module configured to receive and store information that one of a set of one or more external devices is to send the computer system a medical data file that is to be associated with the identity of a specific one of the patients; b) a module configured to receive a medical data file from an external device, together with an identity of the external device that sent it, and to store the medical data file associated with the identity of the external device; c) a module configured to find which patient identity to associate the medical data file with, from the information, and from the identity of the external device that sent the medical data file; and d) a module configured to store the medical data file, associated with the identity of the patient, in the data storage device.

There is further provided, in accordance with an exemplary embodiment of the disclosure, a computer system comprising: a) a medical data acquisition system according to an embodiment of the disclosure; b) the data storage device; and c) a computer or a plurality of connected computers, the same as or different from the computer or plurality of connected computers running the data acquisition software, that runs a software module that provides authorized users with access to medical data files associated with the identities of patients in the data storage device.

There is further provided, in accordance with an exemplary embodiment of the disclosure, a system comprising: a) a computer system according to an embodiment of the disclosure; and b) an external device, adapted to acquire medical data from the patient, and to send a medical data file with the medical data to the computer system, identifying the medical data file as coming from the external device.

Unless otherwise defined, all technical and/or scientific terms used herein have the same meaning as commonly understood by one of ordinary skill in the art to which the disclosure pertains. Although methods and materials similar or equivalent to those described herein can be used in the practice or testing of embodiments of the disclosure, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the disclosure can involve performing or completing selected tasks manually, automatically, or a combination thereof. Moreover, according to actual instrumentation and equipment of embodiments of the method and/or system of the disclosure, several selected tasks could be implemented by hardware, by software or by firmware or by a combination thereof using an operating system.

For example, hardware for performing selected tasks according to embodiments of the disclosure could be implemented as a chip or a circuit. As software, selected tasks according to embodiments of the disclosure could be implemented as a plurality of software instructions being executed by a computer using any suitable operating system. In an exemplary embodiment of the disclosure, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF EXEMPLARY EMBODIMENTS

The present disclosure, in some embodiments thereof, relates to a method of acquiring medical data from a patient using a possibly insecure external device, sending the data over a possibly insecure communications link to a medical computer system, and storing of the data by the computer system associated with the identity of the patient; more particularly, but not exclusively, to the case where the medical data comprises medical images, and the external device is a mobile device.

An aspect of some embodiments of the disclosure concerns a method of sending medical data pertaining to a patient from an external device to a medical computer system, for storage in a data storage device, associated with the identity of the patient. The method is directed to improvements in the functionality of such a medical computer system for acquiring and storing medical data from an external device. The computer system receives information, for example from a user such as a physician or other medical worker, or the computer system infers, that medical data pertaining to that patient will be sent from a set of one or more external devices, including that external device. When the medical data is received, and identified at least as coming from one external device in the set, the computer system is then able to store the medical data associating it with the identity of the patient. Optionally, this is done in a way that improves workflow by the user, by implementing one or more features in how the method is performed. For example, before the external device is used by the user to send medical data the first time, information is optionally sent from the computer system to the external device about how to send the medical data, or the information is obtained by the external device in some other way, and there is no need for the computer system to contact the external device each time medical data is to be sent, but it is sufficient to have one-way communication from the external device to the computer system. Additionally or alternatively, before the external device is used by the user to send medical data the first time, the external device is registered with the computer system as an external device that may be used by that user to send medical data. Then, each time the user makes an acquisition request to send a medical data file from a registered external device, the user need only select the device from a possibly short list of registered devices displayed on a menu. Or, if only one external device has been registered as being used by that user, the computer system optionally assumes that that device will be used, without any need for the user to indicate an external device at all. Alternatively, even if more than one external device is registered as being used by that user, the computer system assumes that any of those devices might be used to send the data file when the user makes an acquisition request, and there is no need for the user to indicate the specific external device that will be used. But a potential advantage of having the user specify which external device will be used, or at least narrowing it down to only some of the external devices registered to that user, is that the other external devices would then be free to be used to send data files for other patients, possibly by other users who share those external devices with that user.

Optionally, the user need not enter information identifying the patient into the external device at all, and need not enter information identifying the patient into the computer system more than once, potentially improving safety by reducing the chance of an error in data entry which will result in the medical data being associated with the wrong patient. Optionally, no information about the identity of the patient, optionally not even indirect information, is provided to the external device, and optionally no information about the identity of the patient, optionally not even indirect information, is sent from the external device to the computer system, potentially helping to protect the confidentiality of the medical data, if the external device, and/or its communication links to the computer system, are not secure.

Optionally, the external device is a mobile device, such as a smartphone, and it communicates with the computer system over a public network, such as a cell phone network or the Internet. Optionally, the medical data comprises one or more medical image files, for example external images of the patient made by a camera on a smartphone. Alternatively or additionally, the medical data comprises non-image data such as blood pressure data, EKG data, EEG data, or DNA sequencing data, obtained for example using portable equipment linked to the external device. Optionally, the medical data is not data of the patient, but data that a medical worker wants to include in the patient's medical record for other reasons, for example data of family members of the patient in a case where the patient is suspected to have a condition that runs in families, or data showing a textbook example of a condition that the patient is suspected to have, for comparison.

Optionally the method is implemented using software running on the computer system, for example software running on the user's personal computer connected securely to a server used for acquiring medical data in a medical computer system, and/or software running on the server. While running this software, the user opens a file for the patient's medical records, and optionally indicates to the computer system that medical data for that patient will be sent from a particular external device, or from one of a set of external devices, and the software then automatically provides the information to the computer system that a medical data file for that patient is going to be sent from that external device or from one of that set of external devices. Optionally, another program, such as a smartphone app, runs on the external device, and prompts the user, or a different medical worker, to use the external device to acquire the data, for example by taking a picture of an external lesion on the patient. The program running on the external device then sends the data to the computer system, optionally automatically, identified as coming from that external device, or at least identified as coming from one of that set of external devices, but optionally with no other information linking the data to the identity of the patient, even indirectly.

Before explaining at least one embodiment of the disclosure in detail, it is to be understood that the disclosure is not necessarily limited in its application to the details of construction and the arrangement of the components and/or methods set forth in the following description and/or illustrated in the drawings and/or the Examples. The disclosure is capable of other embodiments or of being practiced or carried out in various ways.

Figure 1:
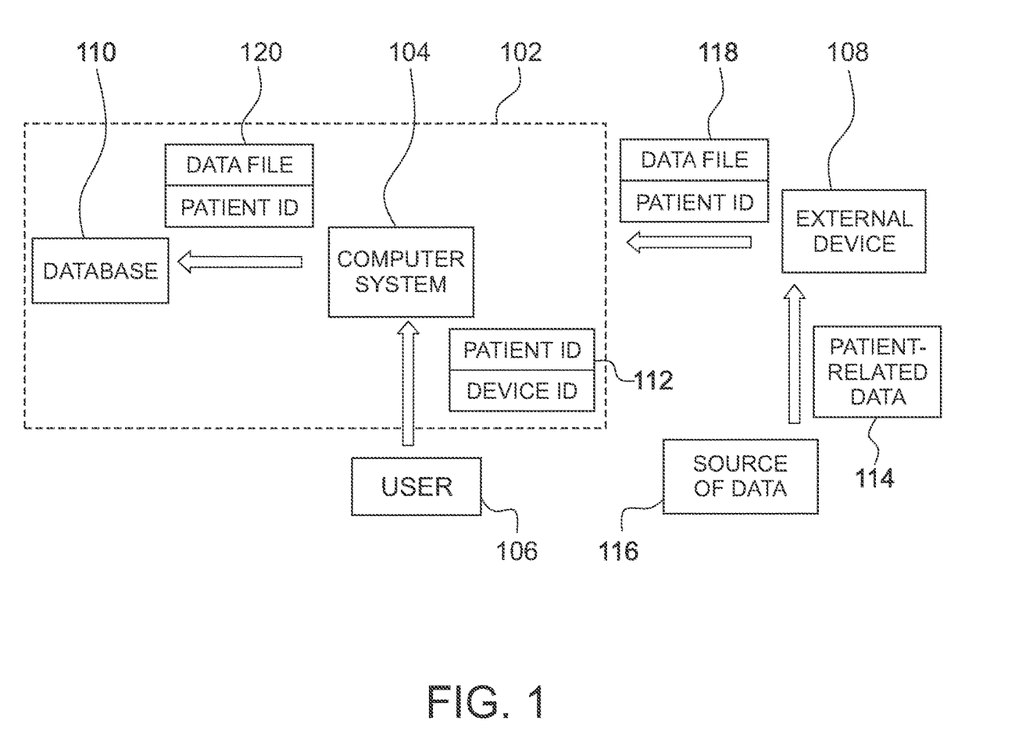
FIG. 1 is a block diagram showing components of a computer system and an external device sending medical data to the computer system, according to an exemplary embodiment of the disclosure.
Figure 2:
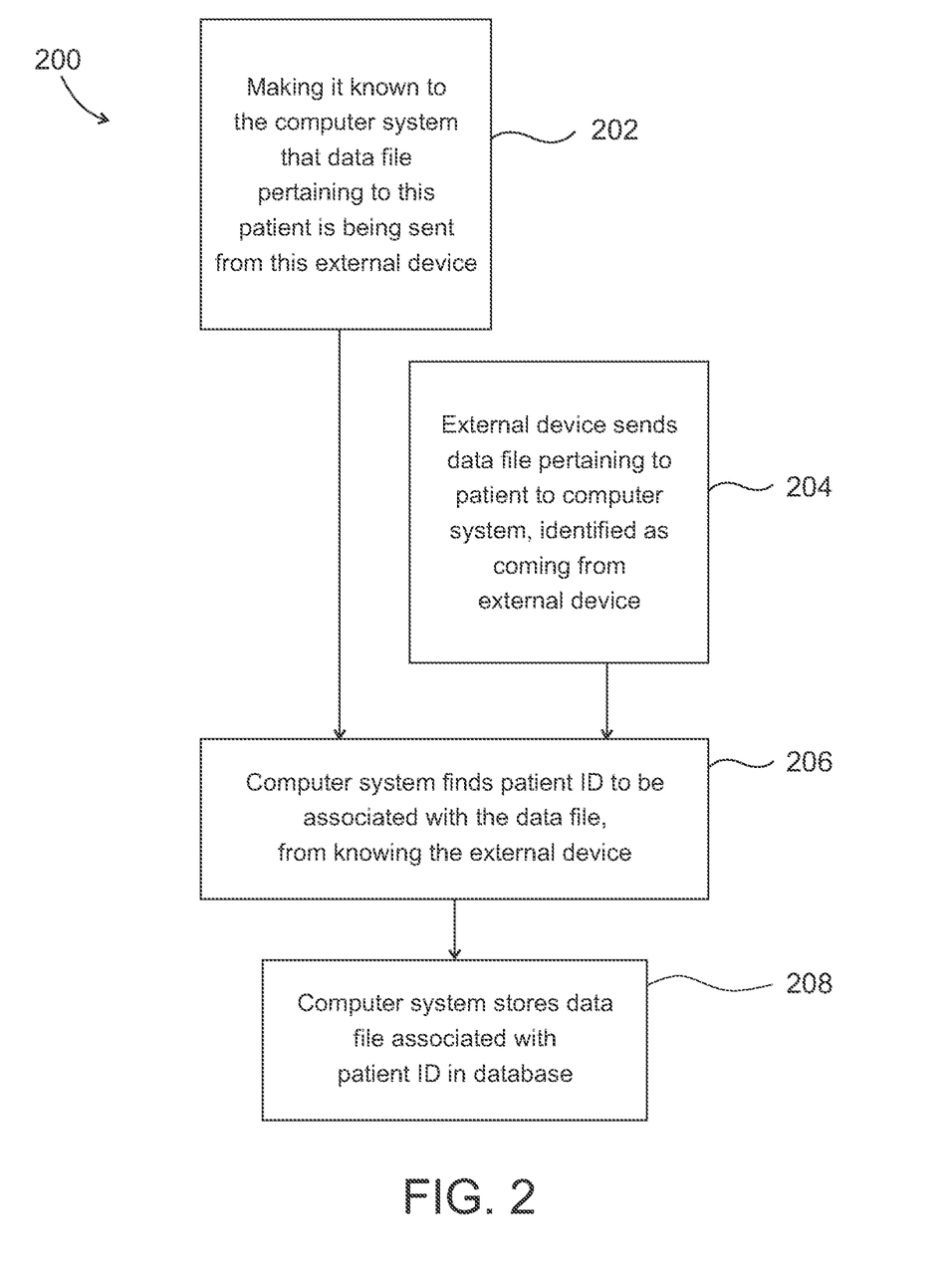
FIG. 2 is a flowchart for a method which could be implemented by the system shown in FIG. 1, according to an exemplary embodiment of the disclosure.
Figure 3:
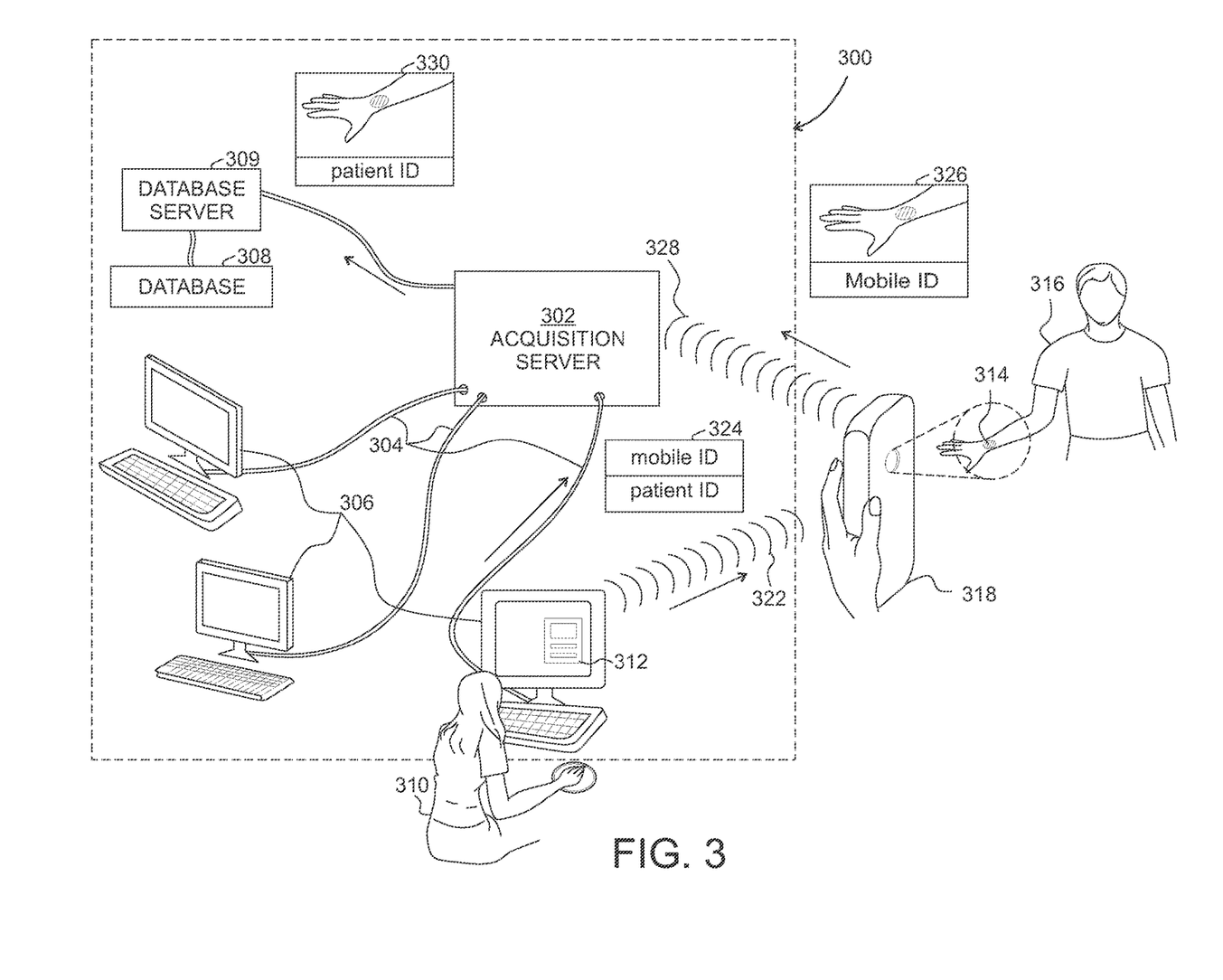
FIG. 3 is a schematic drawing showing further details of the computer system and external device shown in FIG. 1, according to an exemplary embodiment of the disclosure.
Figure 4:
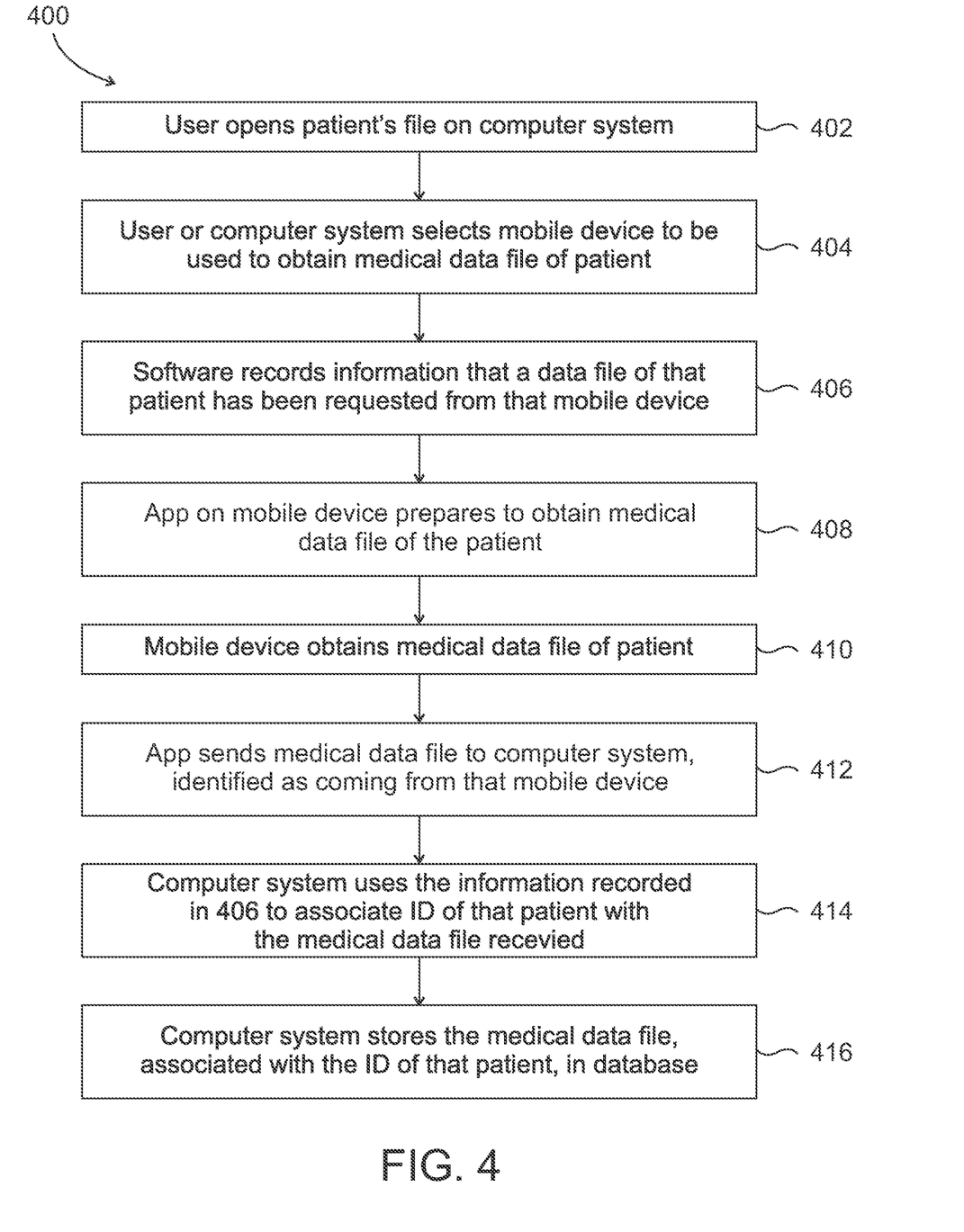
FIG. 4 is a flowchart showing further details of the method shown in FIG. 2, which could be implemented with the system shown in FIG. 1 or FIG. 3, according to an exemplary embodiment of the disclosure.

Referring now to the drawings, FIG. 1 schematically illustrates a system 100 for acquiring medical data pertaining to a patient, sending the data from an external device to a computer system which can find the identity of the patient from the identity of the external device, without any need to provide information about the identity of the patient, even indirect information, to the external device. FIG. 2 shows a flowchart for a method 200 of using system 100 for this purpose. FIGS. 3 and 4 respectively illustrate special cases of system 100 and method 200 for an exemplary embodiment of the disclosure.

In FIG. 1, system 100 includes a medical records system 102 for acquiring, storing, and providing access to patient medical records, with security features that make it suitable for handling confidential medical records associated with different patients. The dashed line shown around records system 102 may be considered a firewall, within which any stored data and internal communications may be considered secure. The records system includes a computer system 104, used by a user 106, for example a medical worker who is permitted to see patient records, and to add new data to them. User 106 may wish to use an external device 108, not part of the secure records system, to acquire data pertaining to a patient and to store it in a data storage device, for example in a database 110 which is part of records system 102, for example an EMR or a PACS. It should be understood that EMR systems and PACS are often self-contained systems with their own servers, provided by outside vendors and not easily modified, and a different server may be used for acquiring data from the external device, but computer system 104 includes all such servers and their communication links with each other. External device 108, for example, is a smartphone with a camera, which may be used to acquire a medical image of the patient, for example an image of a lesion that is visible on the patient's skin. To avoid compromising the confidentiality of patient data, and also to avoid the chance of making an error when manually entering the identity of the patient into external device 108, user 106 optionally may not want to provide any information about the identity of the patient to external device 108, which is outside the firewall of records system 102, and may not want such information to be sent from external device 108 to records system 102 over possibly insecure communication links. But to maintain efficient workflow, it may also be desirable to have external device 108 send the medical data directly and automatically to the records system, and to have the records system automatically associate the data with the identity of the patient. It may also be desirable to do this without any need for two-way communication between the records system and the external device. Furthermore, there may be many medical workers, working for the same organization that maintains the records system, who will frequently be sending medical data pertaining to different patients, from different external devices, to the same records system, without coordinating these activities with each other.

To accomplish these goals, information 112 is made known to computer system 104, for example by user 106 entering an acquisition request into computer system 104, with information that external device 108, or one of a set of external devices that includes external device 108, will send medical data pertaining to a particular identified patient. Alternatively, at least some of information 112 may be inferred by computer system 104 from other information it already knows, for example it may know that user 106 always uses the same external device 108, or only uses certain external devices including external device 108, in which case there will be no need for user 106 to explicitly enter information 112 into computer system 104 as part of the acquisition request, or the user enters information 112 explicitly only if the user is using a different external device than usual. This action is shown as element 202 of flowchart 200 in FIG. 2. User 106, or another medical worker, then arranges for patient-related data 114 to be acquired by external device 108 from a source 116. For example, source 116 is the patient that the data pertains to, and external device 108 acquires the data by taking a picture of the patient, or by making medical measurements of the patient by using a portable device linked to external device 108, for example a portable device for measuring blood pressure, or a portable EKG device. Alternatively, source 116 is not the patient that the data pertains to, but is, for example, a family member of the patient, whose medical data user 106 wants to compare to the patient's medical data, or source 116 is another database which stores medical records of the family member. Alternatively, patient-related data comprises standard textbook images or other kinds of data sets illustrating a medical condition that user 106 wishes to compare to analogous data from the patient, and source 116 is an outside archive storing such standard images or data sets.

Once external device 108 acquires patient-related data 114, the data is sent as a data file 118, identified as coming from external device 108, to computer system 104. This action is shown as element 204 of flowchart 200. Computer system 104 then uses the identity of external device 108, and information 112, to find the identity of the patient that data file 118 pertains to, which is element 206 of flowchart 200. The data is then stored in database 110 as a data file 120 associated with the identity of the patient, which is element 208 of flowchart 200.

FIG. 3 illustrates a medical records system 300 that can receive medical data from external devices, according to an exemplary embodiment of the disclosure. System 300 comprises an acquisition server 302 that runs software for acquiring new records for the medical records system. Server 302 optionally has secure communication links 304 with peripheral devices 306, for example personal computers that are used by different medical workers. System 300 stores and accesses medical records for a generally large number of patients, using one or more databases 308, for example an EMR system for text-based records, and/or a PACS for images. Optionally, the one or more databases each have their own database server 309, that runs software for providing access to the medical records in the database. Optionally, peripheral devices 306 also have direct communication links, not shown in FIG. 3, to database server 309, for the purpose of accessing records. Although the software for accessing records optionally runs instead on acquisition server 302, which would then also serve as a database server, a potential advantage of having a separate acquisition server is that databases, such as an EMR system or a PACS, often are sold as self-contained units with their own servers and operating software included, and it may be easier to implement the method of flowchart 200 with a separate acquisition server, than to modify the software of the database servers. Optionally, acquisition server 302 runs software that communicates with a software module running on the database server that implements the acquisition of new records for the database, and there is no need to make any software or hardware changes in the database or database server. Optionally, requests from peripheral devices 306 to access records in the database are also channeled to database server 309 through acquisition server 302, rather than communicated directly to database server 309.

Although FIG. 3 shows acquisition server 302, peripheral devices 306, database 308 and database server 309 as physically separate devices, optionally the functions of all or some of these separate devices are performed by a single computer, and optionally the functions of some of these devices are divided among more than one physical component, for example the one or more databases may comprise a plurality of separately housed data storage units all in communication with database server 309, and the one or more databases may each come with their own servers. Although communication links 304, and a link between acquisition server 302 and database server 309, and between database server 309 and database 308, are shown in FIG. 3 as hardwired, optionally some or all of them are wireless communication links. Because system 300 is handling patient medical records which are generally considered to be confidential, the components of the system, and the communication links between them, are generally expected to meet some standard of security, that would not necessarily be expected to be met by external devices that system 300 communicates with.

A user 310, for example a physician or another medical worker, wishes to acquire medical data of a patient using an external device, for example using a smartphone to take a picture showing a medical condition of the patient, and to store the data in database 308, associated with the patient's identity, while avoiding possible disclosure of the medical data, identified as pertaining to the patient, outside the secure records system. User 310 accomplishes this task by running a program 312 on one of personal computers 306 which is linked to server 302, or directly on server 302. In the example shown in FIG. 3, user 310, or another person, acquires an image of a lesion 314 on a patient 316, using an external device 318, for example a smartphone or another kind of mobile device with a camera. Alternatively, another kind of medical data is obtained from the patient, for example blood pressure data, ECG data, EEG data, or even DNA sequencing data, obtained with portable equipment linked to a mobile device, for example in the patient's home. Optionally, external device 318 is not a mobile device, but is, for example, a computer that is not part of system 300.

User 310 optionally sends information over a communications link 322, to external device 318, with instructions, for example a phone number or an email address or a URL, that external device 318 should use in order to send the acquired data to system 300. Optionally, this is done automatically, after user 310 enters an acquisition request into system 300, for example into program 312 running on the user's personal computer 306, informing system 300 that external device 318 is going to be used to send the data. Alternatively, instructions for sending the acquired data to system 300 are entered into external device 318 manually, for example by user 310. Alternatively, for example if external device 318 is used for sending such medical data only to system 300, external device 318 already knows how to send the data to system 300, and there is no need to send such instructions each time external device 318 is going to be used to acquire and send data. Optionally, such instructions are sent to external device 318 only once, as part of a process for registering external device 318 with system 300, before it is used the first time to acquire and send data to system 300, as will be described below in FIGS. 5 and 6.

Because external device 318 is not part of system 300, communications link 322 cannot necessarily be considered secure, or at least any security features it has are not generally under the control of system 300. For example, communications link 322 optionally comprises a cell phone network, or the internet. This is illustrated schematically in FIG. 3 by showing possibly insecure external communication links as wireless links, and by showing secure communication links within system 300 as hardwired links, although any of the links are optionally wireless and optionally hardwired.

User 310 optionally sends an acquisition request to system 300, for example through program 312, informing system 300 that medical data for a patient will be acquired and sent to system 300 from an external device. Optionally, for example as part of the acquisition request, user 310 enters into system 300 information 324, for later use by system 300, that this medical data will pertain to patient 316 and will be sent from external device 318, or from one of a set of external devices that includes external device 318. Information 324 is optionally entered into program 312, and is sent, for example, to server 302, and/or is saved on the peripheral computer 306 that program 312 is running on, or on another component of system 300.

Alternatively, some or all of information 324 is not entered explicitly by user 310, but is made known to system 300 in a different way, for example it is inferred from information that personal computer 306, or another part of system 300, already has. For example, user 310 optionally enters the identity of patient 316 into program 312 as part of a procedure for accessing the medical records of patient 316, or to register the fact that user 310 was dealing with patient 316 at that time, before sending the acquisition request to system 300. In this case, optionally program 312 learns the identity of patient 316 in that way, and there is no need for user 310 to enter the patient's identity into program 312 again, for use in information 324. As another example, in some embodiments of the disclosure, one or more external devices, including external device 318, are registered in advance with system 300, as external devices that may be used by user 310; details of how such registration is done are given below in FIGS. 5 and 6. If external device 318 is the only external device registered with system 300 as being used by user 310, then optionally program 312 infers that external device 318 is the external device that will be used to send the data, and this fact is included in information 324, without any need for the user to explicitly enter that information. Alternatively, there are two or more external devices registered as being used by user 310, optionally a relatively small number of external devices, and program 312 lists those registered external devices on a menu, and user 310 selects the external device that will be used. Alternatively, program 312 infers that one of external devices registered to user 310 will be used to send the data, and the user need not specify which one will be used. In some embodiments of the disclosure, external device 318 belongs to patient 316, for example it is a smartphone belonging to patient 316, and it is regularly used to acquire and send data of patient 316 to system 300, but not data of any other patient. The data, for example, is acquired in the patient's home, by the patient, or by a visiting medical worker. If this fact is made known to system 300 in advance, for example if external device 318 is registered in advance as being used exclusively for patient 316, then optionally system 300 infers the identity of the patient from the identity of the external device, or infers the identity of the external device from the identity of the patient, when user 310 sends an acquisition request to system 300, and it is not necessary for user 310 to explicitly enter the identity of the patient and the identity of the external device in information 324.

The foregoing options all have the potential advantage that it may take little or no additional effort, on the part of user 310, to make known to system 300 that medical data pertaining to patient 316 will be sent to system 300 from external device 318.

If the user sends an acquisition request specifying a patient, and if the user indicates, or system 300 infers, that the data file might be sent by any external device in a set of two or more external devices, then optionally a special protocol is initiated by system 300 if data files are received from two different external devices in the set, within a short enough time interval. Receiving data files from two different external devices in these circumstances might raise a question about whether there is some error in information 324, or another acquisition request sent by the user which did not go through properly, in which case associating all the files with the same patient might result in a data file being associated with the wrong patient in the database. To handle this situation, system 300 might always associate both data files with the patient specified in the acquisition request, or might not associate any of the data files with the specified patient, or might only associate the first data file received with the specified patient. Whatever action is taken, system 300 optionally also issues an alert to the user that there is a potential problem, and requests the user to verify which data file should be associated with each patient. A similar question might arise if two acquisition requests for different patients are received within too short a time interval, and if there is some overlap in the specified external devices for the two acquisition requests, and both data files are received from external devices that are specified in both acquisition requests. In this situation, system 300 might always associate the data files with the specified patients according to the order the acquisition requests are received and according to the order that the data files are received, or might not associate any of the data files with patients, and in any case optionally issues an alert to the user to verify which data file should be associated with which patient.

In some embodiments of the disclosure, when system 300 knows that the data is going to be sent from external device 318, program 312, or another component of system 300, sends a request to external device 318 for the data file, optionally telling external device 318 where to send the data file, for example if external device 318 does not already know where to send it, and optionally telling a program running on external device 318, for example a smartphone app, to acquire the data and to send it. Alternatively, no information is sent from system 300 to external device 318, but a program on external device 318 that is used to acquire and send the data is activated manually, for example, by user 310, or by another person. A potential advantage of not having two-way communication between system 300 and external device 318, but only the one-way communication of external device 318 sending the data to system 300, is that there is no need to design and run a compatible two-way communications protocol between system 300 and external device 318, and there is no need for user 310 to wait for such a two-way communications link to be established, before using external device 318 to acquire and send the data.

Once information 324 has been made known to system 300, user 310 or another user, for example a nurse, or the patient, uses external device 318 to acquire data and create a data file of the patient, for example to create an image file 326 of lesion 314. External device 318 then sends image file 326 over a communications link 328, for example a cell phone network or the Internet, to system 300, for example to server 302, or to the peripheral computer 306 that program 312 is running on. If external device 318 does not already know where to send file 326, then optionally the user provides this information to external device 318. But it is potentially advantageous if there is no need for the user to provide that information, and if external device already knows where to send file 326, either because that information is provided by system 300 each time data files are going to be sent, or because external device always sends such files to a same address associated with system 300. Image file 326 is identified as coming from external device 318, but optionally no other information is included with image file 326 that could reveal the identity of patient 316, optionally not even indirectly. In some embodiments of the disclosure, file 326 is not an image file, but a different kind of data file, for example a file with blood pressure data of patient 316, as will be described below.

Server 302, or another component of system 300 that has access to both image file 326, with the identity of external device 318, and information 324, then uses the identity of external device 318, and information 324, to deduce the identity of patient 316. An image file 330, including image file 326 associated with the identity of patient 316, is then sent to database server 309 and stored in database 308.

In FIG. 4, flowchart 400 illustrates a special case of method 200 used in an exemplary embodiment of the disclosure, using system 300. At 402, the user initiates a procedure on system 300 to indicate that the user is dealing with patient 316, including entering an identifier for the patient, optionally using program 312. The procedure is optionally one that the user would initiate whenever dealing with a patient, for example to open access to the patient's records, or to record the fact that the user saw that patient at that time, and would not require an extra action on the part of the user. At 404, the user uses program 312, running on some component of system 300, to send an acquisition request to system 300, informing system 300 that a medical data file for the patient will be sent from an external device, for example a mobile device. The identity of the external device to be used, or of a set of external devices that might be used, is provided by either the user or the system. For example the user enters a unique identifier for the external device, for example a mobile device ID, a MAC address, a mobile phone number, an email address, or a URL address, into program 312, or the user selects the external device from a menu of all such devices, registered as being used by that user, provided by program 312. Or the system identifies the device, or a set of devices, without the need for user input. For example, the system infers that external device 318 is going to be used because it is the only external device registered on system 300 as being used by that user, or the only external device registered as being used for that patient, or because it was registered as the default device for that user, or for that patient. Or, the system infers that one of a plurality of external devices registered as being used by that user, and/or registered as being used for that patient, will be used. If the external device is identified by an email address, then optionally the system only expects the data file to be identified as coming from that email address, even if there is more than one external device using that email address, and even if the system does not know which external devices or how many different external devices use that email address to send files.

At 406, program 312 records information 324 that a data file for patient 316 has been requested from external device 318 or from one of a set of external devices that includes external device 318. Optionally, program 312 assumes that the data file is for patient 316 because the user initiated a procedure to open access to the medical records for patient 316, at 402, or has otherwise initiated a procedure for dealing with the patient, for example entering information on a log that the user is now dealing with that patient. Optionally, if the procedure for dealing with a patient is still active for more than one patient on the user's personal computer, then program 312 optionally assumes that the data file is for the patient for whom the procedure has been initiated by the user most recently, or program 312 requests input from the user to indicate which of a plurality of patients the data file is for. Alternatively, the user always explicitly enters information to program 312 specifying which patient the data file is for. But assuming that the patient is one for whom the user has recently initiated a procedure, has the potential advantages that the user does not have to take the time and effort to enter the identity of the patient again, and that there is no concern that the user will make a mistake in identifying the patient.

In information 324, external device 318 is identified, or each of a set of external devices that includes device 318 is identified, for example, by a mobile device ID, a MAC address, a URL address, a mobile phone number, or an email address. An email address may be used for identifying external device 318, for example, if external device 318 sends data file 326 to system 300 using email, while a phone number may be used to identify device 318 if it sends data file 326 using a communications protocol that operates over a cell phone network, for example if data file 326 is sent as an MMS message. A URL address or a MAC address may be used to identify external device 318, if it has one. If an email address is used to identify device 318, then optionally no other external device communicates with system 300 using the same email address, at least not for obtaining data files pertaining to a different patient, using the same program 312, while system 300 is still waiting for data file 326. The identity of external device 318, associated with data file 326, is then sufficient by itself for system 300 to uniquely identify the patient to be associated with data file 326.

At 408, a program running on external device 318, for example an app running on a mobile device, prompts user 310, or another person, to use external device 318 to acquire the data file. For example, user 310 may be a physician who takes a picture of lesion 314, or a nurse may take a picture of lesion 314, perhaps in an examining room while user 310 is sitting by a desktop computer in an office nearby, or the patient or a family member or a visiting medical worker may take the picture, for example at the patient's home, while talking to user 310 by phone. Alternatively, external device 318 is connected to a portable medical instrument, such as a blood pressure measuring device, or a fever thermometer, or an EKG or EEG device, or a device for measuring blood oxygen or other blood components, or a device for DNA sequencing of the patient's cells or of pathogens, and prompts user 310 or another user to acquire a data file of the patient, showing blood pressure, an EKG trace, etc., from the portable medical instrument. Such an arrangement may be especially useful if the patient is located at home, or at any location remote from system 300, where it may not be possible to use a medical instrument that is connected by a fixed internal communications link to system 300.

At 410, external device 318 acquires the data file from the patient. At 412, external device 318 sends data file 326 over communications link 328 to system 300, for example to server 302, or to the peripheral device 306 that was used to make the acquisition request, or to another component of system 300 that has access to information 324. The data file is identified as coming from external device 318, or, in some embodiments of the disclosure, as coming from one of a set of external devices, for example from any external device using a particular email address to send data files, but optionally there is no other information provided with the data file that can be used, even indirectly, to identify the patient, and in some embodiments of the disclosure it would not even be possible for external file 318 to include such information on the identity of patient 316, because no information on the identity of patient 316, not even indirect information, is ever sent to external device 318. Not having device 318 send information with data file 326 that could be used to identify the patient, and not even providing such information to device 318, has the potential advantage that the confidentiality of the patient's medical data would not be compromised by the transmission of data file 326 over communications link 328, even if communications link 328 is not secure, and even if external device 318 is not secure.

It should be noted that in some prior art methods cited above, information linking a medical data file to the patient's identity is sent to a server by an external device, in some cases in a coded form such as a session identifier, and in those methods there may be a greater potential for the patient's confidential medical data to be compromised. In addition, in any method where explicit or coded information about the patient's identity is sent by the external device to a computer system, that information must either be entered into the external device manually by a user, or must be sent to the external device by the computer system. In either case, the procedure is potentially slowed down, decreasing the workflow of the user, since it takes time for the user to enter patient information manually into the external device, and since it takes time for computer system to establish contact with the external device and to verify that the information has been received, and meanwhile the user has to wait, before using the external device to acquire the data. In addition, if the user has to enter information about the identity of the patient manually into the external device, this could potentially increase the chance that the data file will be stored with the wrong patient identity, if the user makes a mistake in entering the information about the identity of the patient into the external device.

Optionally, external device 318 sends data file 326 to system 300 automatically, once data file 326 is acquired, for example under the control of the app or other program running on device 318, without the need for user 310, or another user operating external device 318, to do anything. Potentially such an arrangement increases workflow of medical personnel, since once data file 326 is acquired, there is no need for further input from medical personnel, who can go on to their next patient. Optionally, user 310, or a different user operating external device 318, can examine the data file, and make sure it is good, before external device 318 sends the data file to system 300, and if the data file does not seem to be good, then another data file can be acquired from the patient immediately, while the patient is still available.

At 414, system 300 uses information 324, which was recorded at 406, together with the identification of the external device that was sent with data file 326, to find the identity of the patient for whom the data file pertains. If information 324 identifies which external device 318 will send that data, then system 300 associates a medical data file coming from external device 318, for example the next such data file received after information 324 is obtained, with the identity of the patient specified in information 324. If information 324 only specifies a set of external devices that might be used to send the data file, then system 300 associates a medical data file sent by any of the external devices in the set, for example the next such data file received, with the identity of the patient specified in information 324. Finding the identity of the patient is optionally done by server 302, or by a peripheral device 306, for example a peripheral device on which program 312 was running, and which the user used to make an acquisition request. Optionally, the determination of the identity of the patient is done as part of program 312. If the data file with the identification of the external device is sent to a different component of system 300 than the component where information 324 is stored, then either the identification of the external device, or information 324, or both, are transferred to a different component, so one component has access to both of them. In general, any action that is described as taking place in one component of system 300 may also take place in any other component of system 300 that is capable of performing that action. Especially if different components of system 300, and communications links between them, are secure against breaches of confidentiality of patient data, it may not make much difference which component of system 300 performs a particular action.

The identification of external device 318, and information 324, is sufficient to find the identity of the patient, if external device 318 (or the set of external devices, in the case where information 324 specifies a set of external devices) is only acquiring and sending one data file at a time, or at least is acquiring and sending data files for only one patient at a time. Once the patient associated with the data file has been identified by system 300, information 324 is optionally deleted, or marked as already used, and user 310 is free to use the same external device (or any external device in the set) for acquiring and sending another data file, even for a different patient, after new information 324 is recorded.

It is noted that in some prior art cited above, that may include an external device sending a medical data file to a server, the identity of the patient is not found by the server from the identity of the external device, but from other information about the patient's identity, coded or uncoded, that the external device sends to the server, such as a session identifier.

At 416, data file 326 is stored in database 308, optionally through database server 309 if there is a separate database server, and labeled as associated with the identity of patient 316, as found at 414.

It is noted that, although the data associated with patient 316 is typically data taken from patient 316, such as an image of a part of the body of patient 316, or an EKG trace taken from patient 316, medical data taken from other people might be associated with patient 316 as well, in database 308. For example, a data file associated with patient 316 might have data taken from a family member, if the patient's physician believes that the patient might have a condition that runs in families, and wishes to compare the patient's data to data from family members. Or, a data file associated with a patient might be taken from a library of standard data files, to illustrate a textbook case of a medical condition that the physician wishes to compare to analogous data from the patient.

Figure 5:
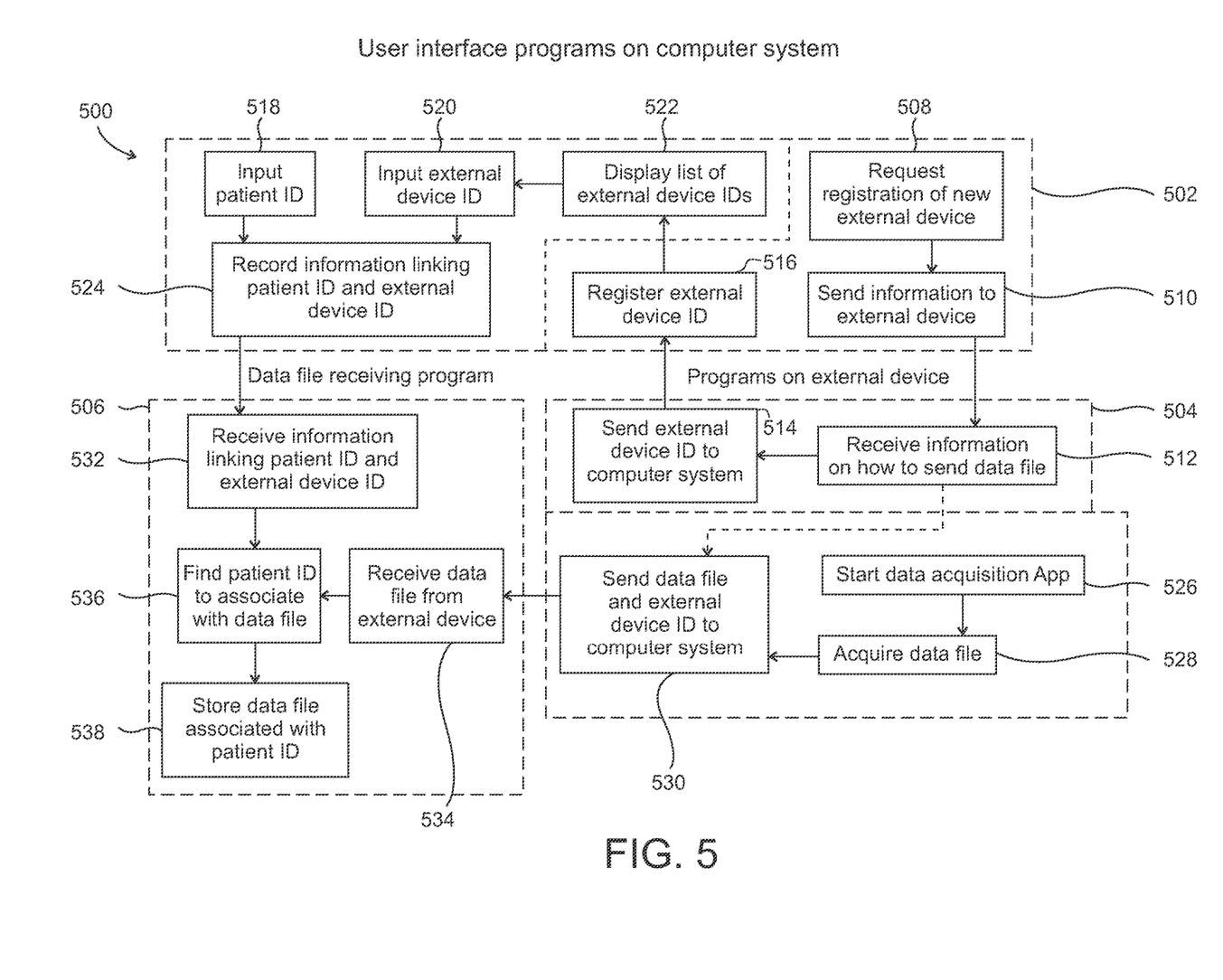
FIG. 5 is a block diagram for software running in a computer system and in an external device that could be used in implementing the method shown in FIG. 2 or FIG. 4, with the system shown in FIG. 1 or FIG. 3, according to an exemplary embodiment of the disclosure.

FIG. 5 shows a flowchart 500 for computer programs, such as program 312, running on system 300, and on external device 318, in an exemplary embodiment of the disclosure. Dashed lines are used to indicate different programs, and programs running on different computers or devices. Programs 502 are two user interface programs running on computer system 300, for example on the user's personal computer that is connected to server 302. Programs 504 are two programs that run on external device 318. Program 506 is a data file receiving program that runs on computer system 300, for example on server 302. Optionally the user interface programs and the data receiving program run on a same component of system 300. In general, especially if different components of system 300 have secure communication links between them, it may not be very important, from a security standpoint, on what component of system 300 a given program runs. Optionally, any programs shown in FIG. 5 as separate programs, that run on a same component of system 300, or on a same device, are implemented as part of the same program, and optionally any functions shown in FIG. 5 as being performed by a same program are implemented in separate programs, running on a same computer or device or on separate computers or devices.

One of programs 502 is a program for registering a new external device, that is going to be used to acquire and send medical data files from one or more patients to system 300. This program communicates with a corresponding program running on the external device that is being registered. Although the functions performed by these programs are optionally performed every time a data file is acquired and sent for a different patient, registering the external device in advance has the potential advantage that these functions can only be performed once, and need not be performed every time a data file is acquired and sent, saving time.

At 508, a user requests registration of a new external device. At 510, information is sent from system 300 to the external device. Optionally, this information is sent by means of a machine readable visual code, such as a linear bar code or matrix bar code, for example a QR Code®, displayed by system 300 and scanned by the external device, as described below in FIG. 6. The information optionally includes information on how the external device should send the data file to system 300. This information is received by the program running on the external device, at 512. At 514, the external device sends a unique external device identifier to system 300. Optionally instructions for how to send the device identifier are included in the information received at 512, and optionally the address for sending this information, for example a phone number, email address, or URL address, is the same as the address for sending the data file to system 300. System 300 receives the device identifier at 516, and registers the external device as one that may be used in the future by that user, for acquiring and sending data files of patients. In some embodiments of the disclosure, the program gives the user the option of indicating that the registered device should be listed as the default device of the user, even if other alternative external devices are also registered as devices that may be used by that user. Optionally, if the external device is, for example, a smartphone that belongs to a particular patient, the external device is also optionally registered as belonging to that patient, and as only being used for sending data files for that patient, and possibly as being the default device to use for sending files for that patient. Optionally, when the external device is registered, system 300 also lists an alias for the external device, such as "Dr. Smith's cell phone," received for example from the user at 508, or entered earlier by the user on the external device and received from the external device together with the device identifier at 516.

Another user interface program running on system 300 is used for initiating the acquisition and sending of a data file for a patient by an external device. At 518, the identity of the patient is made known to computer system 300. Optionally this is done by entering a unique identifier for the patient into a user interface, specifically for the purpose of acquiring a data file for that patient from an external device. Here and elsewhere, the user interface optionally uses auto-fill, or a drop-down menu listing expected choices, which has the potential advantage of reducing the time and effort necessary for entering the information. Alternatively, the program infers the identity of the patient, for example because the user has already entered an identifier for the patient, as part of a process of initiating a procedure for the patient, for example to gain access to the patient's records, or to log the time at which the user started dealing with the patient. A potential advantage of using such an indirect way to identify the patient is that the user, for example a physician seeing the patient, may in any case have to enter the identifier for the patient when initiating the procedure, and the user may save time by not having to enter the identifier for the patient again.

At 520, the identity of the external device is made known to system 300, or the identities of a set of external devices that might send the data file is made known to system 300. Optionally, the user enters a unique identifier for the external device, for example a mobile device ID, a phone number, an email address, a URL address, or a MAC address, into the user interface program, for example as part of making an acquisition request. Alternatively, the user interface program displays to the user a menu listing one or more external devices which have previously been registered at 516 as being used for this purpose by the user. Optionally, the menu lists descriptive names for the external devices, for example, "Dr. Smith's cell phone," or "Patient John Doe's cell phone," or "Default device," that are aliases for external device identifiers that were used for registering the external devices at 516. Optionally, if only one external device is registered as being used by the user, then the program assumes at 520 that that external device is the one that will be used this time. Alternatively, if the patient is listed in system 300 as having an external device that is always used to acquire and send medical data files, then the program assumes at 520 that that external device will be used. Optionally, one external device is registered as being the default device for that user, or for that patient, and the program assumes that device will be used, unless the user takes an action to indicate that a different device will be used. In some embodiments of the disclosure, instead of specifying the identity of a single external device at 520, a set of such external devices is specified. In this case, for example, system 300 optionally uses the set of all external devices registered as being used by that user, and/or all external devices registered as being used for that patient, without the need for the user to enter any information about which external device will be used. Or, the user interface program displays a menu listing all the devices registered for that user or for that patient, and the user has the option of selecting more than one of them, if the user is unsure which device will be used. These alternative options have the potential advantage of reducing the time and effort needed for the user to make the identity of the external device known to system 300, potentially improving workflow of the user.

At 524, information linking the identity of that external device, or set of external devices, and the identity of that patient is recorded for later use by system 300, by program 506. Optionally, supplementary information about the data file, for example a part of the body that is being imaged, or conditions in which EKG data is taken, such as exercising or resting, is also added by the user to the information at 524. Additionally or alternatively, such supplementary information is entered into the external device, and is attached to the data file by the external device before it sends the data file to system 300.

Returning to programs 504 running on the external device, at 526 a data acquisition program, for example a mobile device app, is started. At 528, a data file is acquired, for example by using the external device to take a picture of an external lesion or other medical condition of the patient and to save it as an image file, or by using the external device to acquire blood pressure data, EKG data, etc., for the patient, or by using the external device to download or otherwise acquire data from a different person that the user wants to include in the patient's medical record, for example data from a family member of the patient in the case of a suspected genetic disease or contagious disease, or data from a textbook illustrating a medical condition that the user suspects the patient may suffer from. At 530 the data file is sent to system 300, together with the identifier of the external device that was registered at 516. Optionally, the data file is only sent after the user, or another person who is operating the external device, has examined the data file, decided that it is satisfactory, and approves it for sending.

In program 506, running on system 300, for example on server 302, the information linking the identity of the external device and the identity of the patient, recorded at 524, is received at 532. At 534, the data file is received from the external device, together with the identity of the external device. At 536, program 506 finds the identity of the patient to associate with the data file, using the identity of the external device that was received at 534, and the link between the identity of the external device and the identity of the patient that was received at 532. At 538, the data file, associated with the identity of the patient, is stored in database 308.

Figure 6:
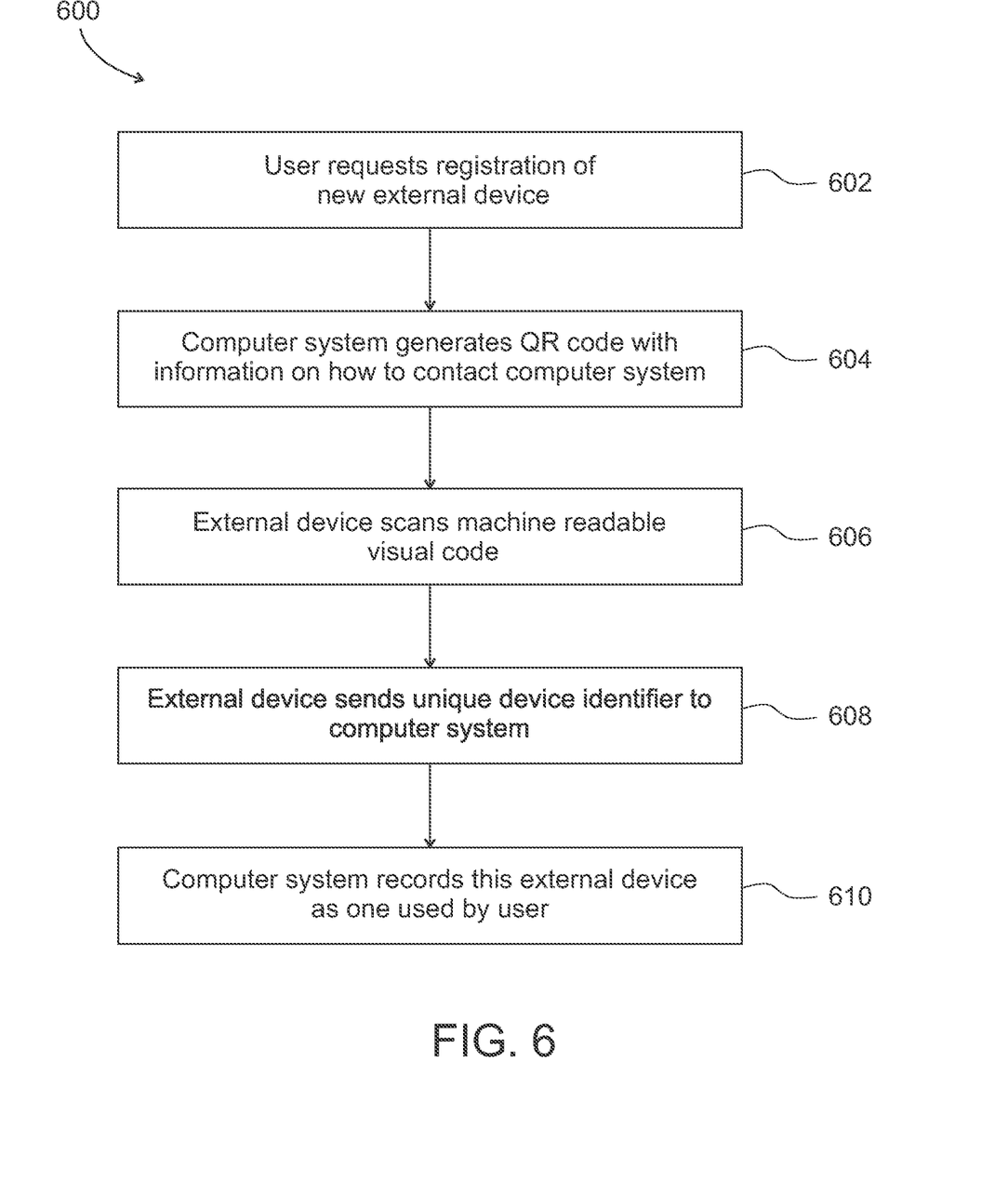
FIG. 6 is a flowchart for a method of registering an external device with a computer system, before using the external device the first time to send medical data to the computer system when performing the method of FIG. 2 or FIG. 4, according to an exemplary embodiment of the disclosure.

FIG. 6 shows a flowchart 600, giving further details of the programs used for registering a new external device, described in FIG. 5. At 602, a user requests registration of a new device. Optionally, this program is initiated at 520 in FIG. 5, when the user sees that the external device that is going to be used is not listed on the menu of already registered devices, or when there are no external devices already registered for that user. Alternatively, this program is initiated by the user, in advance of using the external device to acquire and send any data files, for example in order to save time later when using the external device for the first time to acquire and send data files.

At 604, system 300, or whatever system is running the registration program, optionally generates a machine readable visual code, such as a linear bar code or matrix bar code, with information on how to send data to the system. Using a machine readable visual code for this purpose may be especially useful if the external device is a mobile device, such as a smartphone, and if the external device is physically present in the same room as a display used by the system. At 606, the external device scans the machine readable visual code. At 608, the external device sends a unique device identifier to the system, optionally using the information received on how to send data to the system. Alternatively, the external device only displays the device identifier to the user, and the user manually enters it in the registration program. Optionally, the external device also stores that information, for later use when sending data files to the system. Alternatively, the information on how to send data to the system is entered into the external device in a different way, for example manually by the user, and the machine readable visual code is only used to tell the external device that the system is expecting to receive its unique device identifier, in order to register it. At 610, the system records the external device, identified by its unique device identifier, as one that may be used by the user.

It is expected that during the life of a patent maturing from this application many relevant devices will be developed that can be used to acquire medical data from a patient, and the scope of the term "external device" is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination or as suitable in any other described embodiment of the disclosure. Certain features described in the context of various embodiments are not to be considered essential features of those embodiments, unless the embodiment is inoperative without those elements.

The invention claimed is:

1. A method of sending a data file with medical data pertaining to a patient, comprising one or more of medical images, medical test results, numerical data on vital signs, text-based medical data, and sequencing data, from one or more external devices to a computer system, wherein each of the external devices comprises a device identifier, and storing the data file associated with an identity of the patient, wherein the medical data comprises data of the patient taken with a medical instrument and communicated to the external device, wherein the medical data comprises one or more of pulse data, blood pressure data, EKG data, electrical impedance data, magnetic field data, blood analysis data, spectroscopic data of body tissue, auditory data of the heart, auditory data of the lungs, NMR data, and DNA sequence data, the method comprising:
a) registering the one or more external devices to the computer system prior to acquiring the medical data from the external devices;
b) selecting, at the computer system, at least two of the external devices to be used to acquire the medical data, wherein the selecting causes the computer system to send the selected at least two external devices a request to send the medical data to the computer system as the data file;
c) recording, by the computer system in response to the selecting, an instruction, prior to the data file being sent to the computer system, the instruction including information that the selected at least two external devices will send the medical data pertaining to the patient and a location of where the medical data will be sent;
d) receiving a first data file from a first of the selected at least two external devices and identifying the data file as coming from the first of the selected at least two external devices;
e) receiving a second data file from a second of the selected at least two external devices and identifying the data file as coming from the second of the selected at least two external devices, wherein the second data file is received within a predetermined time interval from receiving the first data file;
f) sending an alert to a user to verify which one of the first data file or the second data file should be associated with the patient;
g) associating the identity of the patient with the one of the first data file or the second data file based on at least the identifying of the one of the first data file or the second data file as coming from the selected at least two external devices, the recorded instruction and an input from the user; and
h) storing, by the computer system, the one of the first data file or the second data file associated with the identity of the patient, in a data storage device.

2. The method according to claim 1, further comprising:
sending, by the computer system to the selected at least two external devices, information on how to send data files from the selected at least two external devices to the computer system, before sending the one of the first data file or the second data file, wherein the selected at least two external devices uses the information on how to send data files when sending the one of the first data file or the second data file.

3. The method according to claim 2, wherein the computer system sending information to the selected at least two external devices comprises the computer system displaying a machine readable visual code to the selected at least two external devices, wherein the machine readable visual code is a QR code.

4. The method according to claim 1, wherein the selecting, at the computer system, the at least two external devices is performed by one of the user or the computer system considering all of the external devices corresponding to the user.

5. The method according to claim 4, further comprising:
for each of the external devices registered to the computer system, the computer system displaying a machine readable visual code to the external device; and
receiving the device identifier from the external device in response to the external device scanning the machine readable visual code.

6. The method according to claim 1, wherein the computer system recording the instruction comprises the user of the computer system entering on the computer system an indication of the identity of the patient, as part of a procedure for the user to get access to medical records of the patient, or for the computer system to record that the user was dealing with the patient at that time, or for both.

7. The method according to claim 1, wherein the computer system recording the instruction comprises the user of the computer system entering an indication of the identity of the patient only once, for sending that one of the first data file or the second data file.

8. The method according to claim 7, wherein the user enters the indication of the identity of the patient on the computer system, and not on the at least two external devices that sends the one of the first data file or the second data file to the computer system.

9. The method according to claim 1, wherein the computer system recording the instruction comprises the user identifying one of the at least two external devices to the computer system.

10. The method according to claim 1, wherein sending the one of the first data file or the second data file from one of the at least two external devices to the computer system is done automatically by one of the at least two external device after the medical data is acquired.

11. The method according to claim 1, wherein the one of the first data file or the second data file is an image file, and acquiring the data comprises using a camera controlled by one of the at least two external devices to make an image of the patient.

12. The method according to claim 1, wherein the computer system uses security procedures to prevent unauthorized transfer or copying confidential patient medical information to outside the computer system, and one of the at least two external devices is outside the computer system.

13. The method according to claim 1, wherein the computer system comprises a server connected to a plurality of peripheral computers used by a plurality of different users, and the computer system recording the instruction comprises the user providing the instruction to one of the peripheral computers.

14. The method according to claim 1, wherein the computer uses security features to prevent the unauthorized transfer outside the computer system of medical data identified as pertaining to the patient, and one of the at least two external devices is outside the computer system.

15. The method according to claim 1, wherein sending the one of the first data file or the second data file comprises sending the one of the first data file or the second data file without information that directly or indirectly identifies the patient, other than information that identifies the one of the first data file or the second data file as coming from one of the at least two external devices.

16. The method according to claim 1, wherein one of the at least two external devices that sends the one of the first data file or the second data file to the computer system has no information directly or indirectly associating the one of the first data file or the second data file with the identity of the patient, when the one of the first data file or the second data file is sent.

17. The method according to claim 1, wherein the medical data comprises non-image data further comprising;
EEG data, or DNA sequencing data;
obtained using portable equipment linked to one of the at least two external devices.

18. A medical data acquisition system for acquiring patient medical records and storing each of them in a data storage device associated with an identity of one of a plurality of patients, wherein the medical data comprises data of the patient taken with a medical instrument and communicated to one or more external devices, wherein the medical data comprises one or more of pulse data, blood pressure data, EKG data, electrical impedance data, magnetic field data, blood analysis data, spectroscopic data of body tissue, auditory data of the heart, auditory data of the lungs, NMR data, and DNA sequence data, including a computer or a plurality of connected computers, running data acquisition software comprising:

a) a module configured to register the one or more external devices to the medical data acquisition system prior to acquiring the medical data from the external devices;

b) a module configured to receive a selection of at least two of the external devices to be used to acquire the medical data, wherein the selecting causes the medical data acquisition system to send the selected at least two external devices a request to send the medical data to the medical data acquisition system;

c) a module configured to record an instruction, prior to receipt of a medical data file, that the selected at least two external devices with a specified identifier will send to the medical data acquisition system the medical data file and a location of where the medical data file will be sent;

d) a module configured to receive a first medical data file from a first of the selected at least two external devices and a device identifier of the first of the selected at least two external devices that sent the first medical data file, and to store the first medical data file associated with the device identifier of the first of the at least two external devices;

e) a module configured to receive a second medical data file from a second of the selected at least two external devices and a device identifier of the second of the selected at least two external devices that sent the second medical data file, and to store the second medical data file associated with the device identifier of the second of the at least two external devices;

f) a module configured to send an alert to a user to verify which one of the first medical data file or the second medical data file should be associated with the patient;

g) a module configured to determine a patient identity to associate the one of the first medical data file or the second medical data file with, based on, at least, the recorded instruction and an input from the user; and h) a module configured to store the one of the first medical data file or the second medical data file associated with the patient identity in the storage device.

19. A computer system comprising:
a medical data acquisition system according to claim 18;
a data storage device; and
a computer or a plurality of connected computers, the same as or different from the computer of plurality of connected computers running the data acquisition software, that runs a software module that provides authorized users with access to medical data files associated with the identities of patients in the data storage device.

20. A system comprising:
a computer system according to claim 19; and
one of the at least two external devices, adapted to acquire medical data pertaining to the patient, and to send the one of the first medical data file or the second medical data file with the medical data to the computer system, identifying the one of the first medical data file or the second medical data file as coming from one of the at least two external devices.

* * * * *